United States Patent [19]

Friedman et al.

[11] Plant 4,232

[45] Apr. 4, 1978

[54] FRENCH PRUNE

[76] Inventors: Martin Friedman; Cora G. Friedman, both of Rte. 1, Box 119, Biggs, Calif. 95917

[21] Appl. No.: 669,504

[22] Filed: Aug. 16, 1976

[51] Int. Cl.[2] ..... A01H 5/03

[52] U.S. Cl. ..... Plt./38

[58] Field of Search ..... Plt./38

[56] References Cited

U.S. PATENT DOCUMENTS

| | | | |
|---|---|---|---|
| P.P. 2,713 | 2/1969 | Vinyard | Plt./38 |
| P.P. 3,862 | 4/1976 | Odier | Plt./38 |

*Primary Examiner*—Robert E. Bagwill

[57] ABSTRACT

This present application for a patent relates to a new asexually developed prune tree of the French type, (to be known as the Friedman French Prune). The tree is large, dense, upright, vase formed, very similar to the regular French Prune tree, but a more vigorous grower, reaching full maturity and bearing fruit at least a year earlier than regular French, well foliated with medium size and textured deep green ovate leaves, well distributed throughout the tree. The tree distinguishes from regular French however by its more vigorous growth, and faster maturity to fruit bearing stage, and the fruit always larger, more abundant and evenly distributed throughout the entire tree. All trees, Friedman French and regular French, were grown in the same orchard, under the same growing conditions for this comparison.

A very productive tree coming to full bloom a few days later (a plus if there is danger of late frost), with fruit maturing to full ripe at least 6 days earlier than regular French prune, consistantly producing a full crop, of large size, medium textured, semi-free stone fruit, having basically the same color skin and flesh as regular French prune, a distinct difference being the shape of the fruit, regular French having a true ovate shape with pronounced cavity. The Friedman French, always a much larger prune, is ovate with a distinct pear shape apex, and a small shallow cavity.

1 Drawing Figure

ORIGIN OF VARIETY AND REPRODUCTION

The present variety of prune (Friedman French) was originally found on a tree in an orchard planted to regular French prunes. Being an experienced orchardist and nurseryman, and specializing in prunes, the difference of this prune was quickly noted. Upon close observation of this prune for about 3 years, noting the consistant heavy bearing of large excellant fruit, budwood was taken and asexually reproduced by budding to Myro 29C rootstock in our nursery. A plot of 30 trees was planted in 1970. These trees received the same care in all respects as regular French trees planted in the same plot. The Friedman French grew profusely, quickly matured, and began to produce large excellent quality fruit. The trees and prunes have proved to be true to the characteristics of the parent prune in all respects.

SUMMARY OF THE VARIETY

The present variety of prune tree, to be known as the Friedman French Prune, is a very vigorous grower being a medium to large, upright dense, vase formed hardy tree (depending somewhat on locality, pruning, and other growing conditions). It has an average number of medium sized, ovate, thick, slightly rugose deep green leaves. It produces a consistently full crop of large variable symmetrical, generally ovate or oblong semi-free stone fruit, well distributed throughout the tree, well spaced along the branches. Fruit ripens 4 to 6 days earlier than the French prune. The skin color is deep blue and flesh color yellow to amber, basically the same colors as regular French prune, the difference being the size and shape of the prune, and the earlier bearing qualities of the tree. Said prune is much larger, ovate with a pear-shape apex and small shallow cavity. It has a smaller ratio of dry-away and a semi-free stone makes this a nice plump tasty dried prune, very adapted to being pitted.

DESCRIPTION OF THE DRAWING

The drawing is an illustration by photographic reproduction in color showing a small limb with leaves and fruit, with two of the fruit cut to show flesh and pit coloration and characteristics.

DESCRIPTION OF THE VARIETY

Tree: Size medium to large, sturdy with vigorous upright growth, size and shape are basically determined by methods of pruning and various growing conditions. Said prune tree is very similar to regular French prune except its being a faster grower, earlier and more productive tree.

Trunk: Medium to large, texture generally smooth, same as regular French tree.

Branches: Stocky, smooth to medium texture, lenticels of medium size and average number.

Leaves: Medium, average length and width. Shape ovate with acute base and tip and medium fine serrated margin. Dark green medium texture. Petiole medium length and shape. Glands of average number, small, globose, light green. Stipules of average number, usually two.

Flower Buds: Conical, pubescent medium size, color white. Tree comes in full bloom several days later than regular French prune.

Fruit: Matures and ripens 4 to 6 days before regular French prune. Size large, form variable symmetrical ovate or oblong to a pear shape at apex. Suture moderately distinct base to apex, with a distinct darker color stripe along suture line when fruit is ripe. Lips not pronounced, moderately equal. Cavity small and shallow. Base truncate and oblique. The fruits are approximately 50% larger, overall, than those of the French prune.

Skin: Medium thick, smooth texture, semi-cling. Down wanting. Bloom plentiful, silver-gray. Basically same in texture and color as regular French prune.

Flesh: Basically same in color as regular French prune, of medium soft texture with tender soft fibers. Juice sweet and plentiful. Flavor rich sweet and pronounced. Aroma mild, almost none. Ripens evenly, eating quality excellent. Tests demonstrate an average firmness of 2.70, a fresh weight of 6.90, a dry weight of 2.43, with 36.7 dry fruit per pound and a 2.83 to 1 dry away.

Stone: Medium size to small, light brown semi-free non-split. Form ellipitical. Base oblique. Hilum average. Apex distinct. Sides generally equal. Surface medium, slightly furrowed. Pits small and wanting.

Uses: As a fresh fruit, canning, but basically for drying. The quality of the dried fruit of the Friedman French is the real difference, and proof of superiority and improvement over the regular French prune, being a larger, plump tasty prune.

These trees were grown and tests made in Butte County (Sacramento Valley), Calif. Some variations may be expected subject to location and other growing conditions, including but not limited to water, fertilization, soil conditions, and methods of pruning, any or all could have some effect on the growth and maturity of tree, as well as size and amount of fruit produced.

We claim:

1. A novel French prune substantially as shown and described, characterized by its dense foliage; upright, vase shaped tree form of medium to large size; its vigorous growth; and its consistent bearing of a profuse crop of large, excellent grade fruit which are particularly adapted for drying.

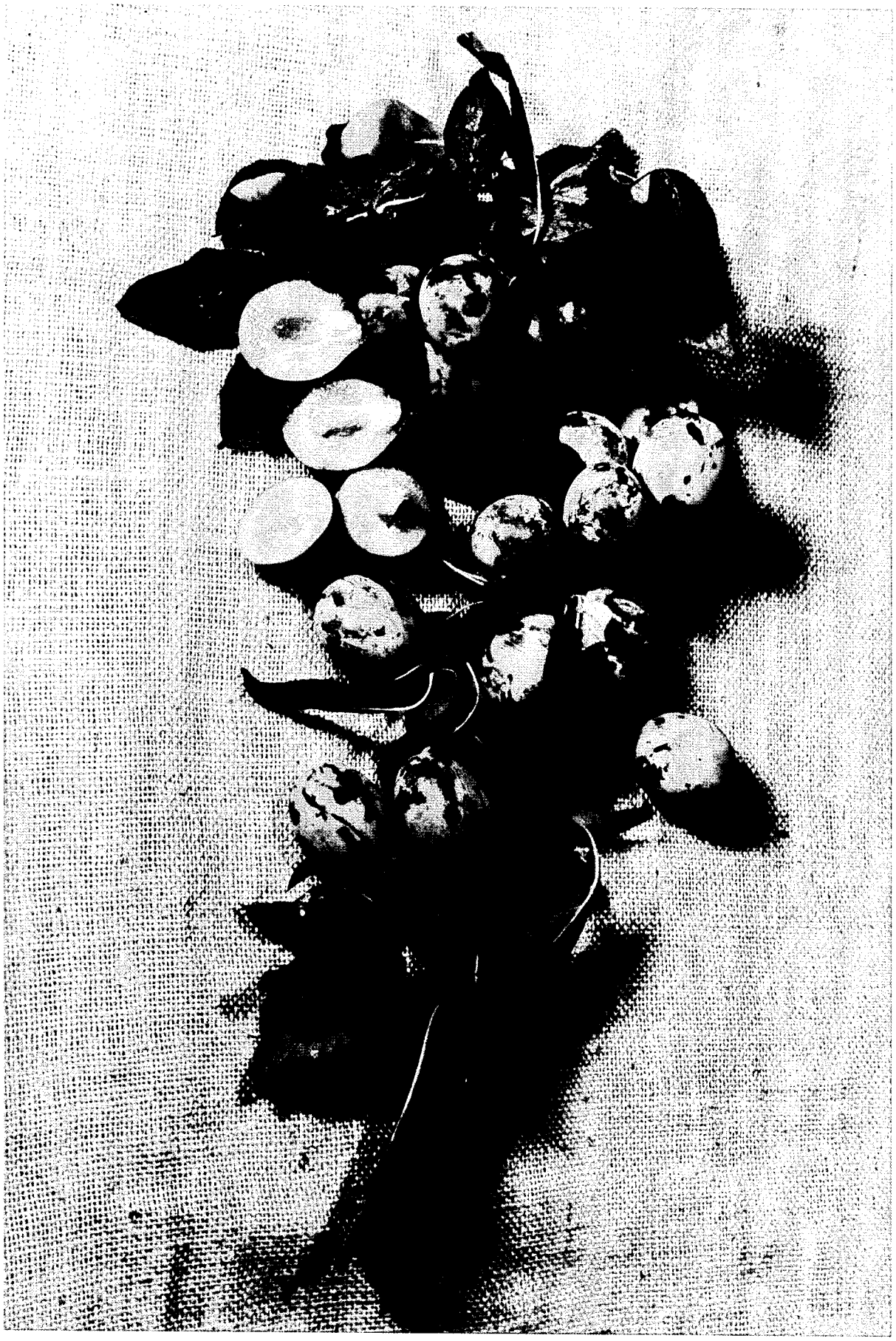

* * * * *